(12) United States Patent
Goto et al.

(10) Patent No.: US 7,087,223 B2
(45) Date of Patent: Aug. 8, 2006

(54) PREVENTIVES AND/OR REMEDIES FOR HYPERPHOSPHATEMIA

(75) Inventors: Takeshi Goto, Tsukuba (JP); Kazuhisa Yoshitake, Tsukuba (JP); Hiroshi Sorimachi, Tsukuba (JP); Kazuteru Moriyama, Tsukuba (JP)

(73) Assignee: Hisamitsu Pharmaceutical Co., Inc., Saga (JP)

( * ) Notice: Subject to any disclaimer, the term of this patent is extended or adjusted under 35 U.S.C. 154(b) by 86 days.

(21) Appl. No.: 10/984,149

(22) Filed: Nov. 9, 2004

(65) Prior Publication Data

US 2005/0084476 A1    Apr. 21, 2005

Related U.S. Application Data

(63) Continuation of application No. 10/221,585, filed as application No. PCT/JP01/01900 on Mar. 12, 2001, now abandoned.

(30) Foreign Application Priority Data

Mar. 13, 2000    (JP)    ................................ 2000-67964

(51) Int. Cl.
*A61K 31/78*    (2006.01)
*A61K 31/785*    (2006.01)
*A61P 3/00*    (2006.01)
*A61P 3/12*    (2006.01)
*A61P 13/12*    (2006.01)

(52) U.S. Cl. ................ 424/78.12; 424/78.1; 424/78.11; 424/78.13; 424/78.14; 424/78.15; 424/78.16; 514/814; 514/824; 514/891

(58) Field of Classification Search .............. 424/78.1, 424/78.11, 78.12, 78.13, 78.14, 78.15, 78.16; 514/814, 824, 891

See application file for complete search history.

(56) References Cited

U.S. PATENT DOCUMENTS

| | | | |
|---|---|---|---|
| 5,414,068 A | 5/1995 | Bliem et al. ................. | 528/288 |
| 5,980,881 A | 11/1999 | Mitsuka et al. ............ | 424/78.1 |
| 6,114,466 A * | 9/2000 | Davankov et al. ........ | 525/332.2 |
| 6,726,905 B1 * | 4/2004 | Mandeville et al. ...... | 424/78.35 |
| 6,858,203 B1 * | 2/2005 | Holmes-Farley et al. | 424/78.11 |

FOREIGN PATENT DOCUMENTS

| | | |
|---|---|---|
| JP | 55102489 A | 5/1980 |
| JP | 06238270 A | 8/1994 |
| JP | 06192111 A | 12/1994 |
| JP | 8-506846 | 8/1996 |
| JP | 9-504782 A | 5/1997 |
| JP | 9-295941 | 11/1997 |
| WO | WO 94/19379 | 9/1994 |
| WO | WO 95/05184 | 2/1995 |
| WO | WO 96/25440 | 8/1996 |
| WO | WO 98/42355 | 1/1998 |

OTHER PUBLICATIONS

Jin to Toseki, 1994, 37, 2:321.

* cited by examiner

*Primary Examiner*—John Pak

(74) *Attorney, Agent, or Firm*—Licata & Tyrrell P.C.

(57) ABSTRACT

Provided in a phosphate ion adsorbent containing a weakly basic anion exchange resin as an active ingredient which aims at providing preventives and/or remedies for hyperphatemia having a high selectivity for the adsorption of phosphate ion and showing an effect of lowering blood phosphorus level and another effect of suppressing phosphorus excretion into the urine.

3 Claims, 5 Drawing Sheets

PREVENTIVES AND/OR REMEDIES FOR HYPERPHOSPHATEMIA

This application is a continuation of U.S. Ser. No. 10/221,585 filed Sep. 12, 2002, now abandoned, which is the U.S. National Phase (371) of PCT/JP01/01900 filed Mar. 12, 2001, which claims the benefit of priority of Japanese Application No. 2000-67964 filed Mar. 13, 2000.

TECHNICAL FIELD OF THE INVENTION

The invention relates to a phosphate ion adsorbent and a preventive and/or a remedy for hyperphosphatemia.

BACKGROUND ART

In patients of renal function disorder, disorder of phosphorus excretion in the urine is observed, and in the early stages of renal failure a renal compensation mechanism works to keep phosphorus homeostasis, temporarily showing increase of phosphorus excretion by inhibiting a phosphorus re-absorption due to increase of PTH (parathyroid hormone). However, it becomes impossible to keep the homeostasis due to aggravation of a renal lesion and lowering of a renal function. As a result, hyperphosphatemia due to reduction of phosphorus excretion and a remarkable increase of PTH occurs. The accumulated phosphorus induces, as direct actions, lowering of blood calcium, acceleration of PTH production/secretion, ectopic calcification and renal osteodystrophy due to suppression of vitamin D activation. Also, as indirect actions via high PTH level, central and peripheral nerve disorders, myocardial disorders, hyperlipemia, saccharometabolism disorders, muscle disorders, growth retardation, cardiac conduction disorders, alveolar diffusion disorders, arteriosclerosis and immunodeficiency are shown. Further, as to phosphorus the aspect as a uremic substance and its direct or indirect involvement for complications of renal failure are known (Jin to Toseki, 37, 2: 321, 1994).

Even if treatment is changed to a dialysis therapy due to renal failure, the above disease conditions and complications continue unless the phosphorus homeostasis is maintained. Consequently, treatment of hyperphosphatemia is essential for dialysis patients of renal failure or patients before dialysis. At present, in the treatment of hyperphosphatemia a diet therapy or an oral phosphorus adsorbent are used. In the diet therapy low protein diet is used, though the intake for long period is difficult, and protein intake of a certain degree is unavoidable, wherefore the effect to lower phosphorus in blood cannot necessarily be expected.

As oral phosphorus adsorbents, mainly three types in the following are currently used.
1) Aluminum preparation (aluminum hydroxide)
2) Calcium preparation (calcium carbonate, calcium acetate)
3) Magnesium preparation (magnesium carbonate)

In 1) side effects of aluminum encephlopathy and aluminum osteopathy due to aluminum absorption are problems; in 2) the adsorbability is inferior compared with the aluminum preparation, and additionally the dose is also high, giving a problem of inducing hypercalcemia due to calcium absorption; further, in 3) there is a problem of inducing hypermagnesemia as in the calcium preparation.

Methods for using an anion exchange resin as an oral phosphorus adsorbent have been reported in recent years. In JP, A, 9-504782 (WO95/05184) an anion exchange resin in which polyallyl amine is crosslinked with epichlorohydrin is reported as a phosphoric acid adsorbent. Also, in JP, A, 8-506846, WO96/25440, it is reported that the anion exchange resin having a guanythidyl group selectively adsorbs phosphoric acid. Further, in JP, A, 9-295941, 2-methylimidazole-epichlorohydrin copolymer and cholestyramine which are bile acid adsorbents are applied as oral phosphorus adsorbents. However, all have a defect that use of a high dose is necessary because of a remarkable reduction of phosphate absorption.

As described above, in a currently carried out hyperphosphatemia treatment, bad effects are concerned in any method. Therefore, the present situation is such that a better remedy for hyperphosphatemia has not been found out up to now.

On the other hand, although it is known that a weakly basic anion exchange resin known under the trade name, for example, such as Ionac A-365 (Sybron Chemicals Co.) is used to remove hydrochloric acid in an aqueous system and a non-aqueous system, there has been no report to date in which this is used as a phosphoric acid adsorbent.

DISCLOSURE OF THE INVENTION

The invention is accomplished in view of the problems of the above prior art, and is to provide a preventive and/or a remedy for hyperphosphatemia having a high selectivity toward a phosphate ion adsorption action, further having a lowering action of blood phosphorus concentration and a lowering action of urinary phosphorus excretion.

The inventors made extensive researches to solve the above problems and found out that a weakly basic anion exchange resin, which was only used as main uses for removal of hydrochloric acid in an aqueous system and a non-aqueous system, surprisingly has a phosphoric acid adsorption action, a lowering action of blood phosphoric acid concentration and a lowering action of urinary phosphorus excretion, and accomplished the invention.

Namely, the invention relates to a phosphate ion adsorbent comprising as an active ingredient a weakly basic anion exchange resin.

Also, the invention relates to the above phosphate ion adsorbent, characterized in that the weakly basic anion exchange resin is a copolymer containing as monomer components an acrylic acid type compound having a tertiary amino group and divinylbenzene.

Further, the invention relates to the above phosphate ion adsorbent, characterized in that the copolymer further contains as monomer components one or more components selected from the group consisting of acrylonitrile, vinylimidazole, vinylhistidine, vinylpyrazine and diaminodiphenylmethane.

The invention also relates to the above phosphate ion adsorbent, characterized in that the weakly basic anion exchange resin has porous bead structure.

Also, the invention relates to the above phosphate ion adsorbent, characterized in that the weakly basic anion exchange resin is Ionac A-365 (trade name; Sybron Chemicals Co.).

Further, the invention also relates to a preventive and/or a remedy for hyperphosphatemia, characterized in that it contains the above phosphate ion adsorbent.

A phosphate ion adsorbent and a preventive and/or a remedy for hyperphosphatemia according to the invention not only can overcome bad effects shown in usual weakly basic anion exchange resins and the aluminum, calcium and magnesium preparations that have been used as a preventive and/or a remedy for hyperphosphatemia, but also have an extremely high selectivity toward a phosphorus adsorption action compared with oral phosphorus adsorbents reported so far in which anion exchange resins are used.

As described above, considering that in general, a weakly basic anion exchange resin is a resin that has been used up to now at the industrial level for the purpose of decoloring, demineralization or hazardous substance removal for solvent, a supplied water or a waste water, the effect attained by the invention is totally surprising.

Weakly basic anion exchange resins used in the invention typically have as its main backbone copolymers of an acrylic acid type compound, which have a tertiary amino group, for example, such as acrylamide or acrylate, and divinylbenzene, and further may contain as other monomer components acrylonitrile, vinylimidazole, vinylhistidine, vinylpyrazine, diaminodiphenylmethane or the like further in a range that it is pharmaceutically acceptable and does not reduce the effect. Preferably they are weakly basic polyacrylate type resins having porous bead structure.

Although preparation of a weakly basic anion exchange resin used in the invention can be carried out by a conventional method known by publications, etc., specifically it can be carried out by copolymerization of a monovinyl monomer such as acrylic acid or its alkyl ester and divinylbenzene and reaction of this copolymer with polyalkylene polyamine. Additionally, this copolymer can be copolymerized with other monomers such as acrylonitrile, vinylimidazole, vinylhistidine, vinylpyrazine or diaminodiphenylmethane in a range that it is pharmaceutically acceptable and does not lose the effect.

Illustrative of such a weakly basic anion exchange resin is, for example, Ionac A-365 (trade name; Sybron Chemicals Co.) which is being marketed with the main use for removal of, hydrochloric acid in an aqueous system and a non-aqueous system.

The phosphoric acid adsorbent and the preventive and/or the remedy for hyperphosphatemia according to the invention lower blood phosphorus concentration and urinary phosphorus excretion. Therefore, the preventive and/or the remedy for hyperphosphatemia according to the invention are expected to have a preventive and/or therapeutic effect toward a renal function disorder, chronic renal failure, dialysis, hypocalcemia, excess secretion of parathyroid hormone (PTH), suppression of vitamin D activation, ectopic calcification or the like wherein hyperphosphatemia is considered to be the cause of disease. Further, the preventive and/or remedy for hyperphosphatemia of the invention are expected to exert a remarkable preventive effect and/or therapeutic effect toward PTH increase due to hyperphosphatemia, secondary hyperparathyroidism via vitamin D lowering, renal osteodystrophy, uremia, central and peripheral nerve disorders, anemia, myocardial disorders, hyperlipemia, saccharometabolism disorders, itch, dermal ischemic ulcer, tendon rupture, reproductive dysfunction, muscle disorder, growth retardation, cardiac conduction disorders, alveolar diffusion disorders, arteriosclerosis, immunodeficiency, etc.

MODE FOR CARRYING OUT THE INVENTION

Figure 1:
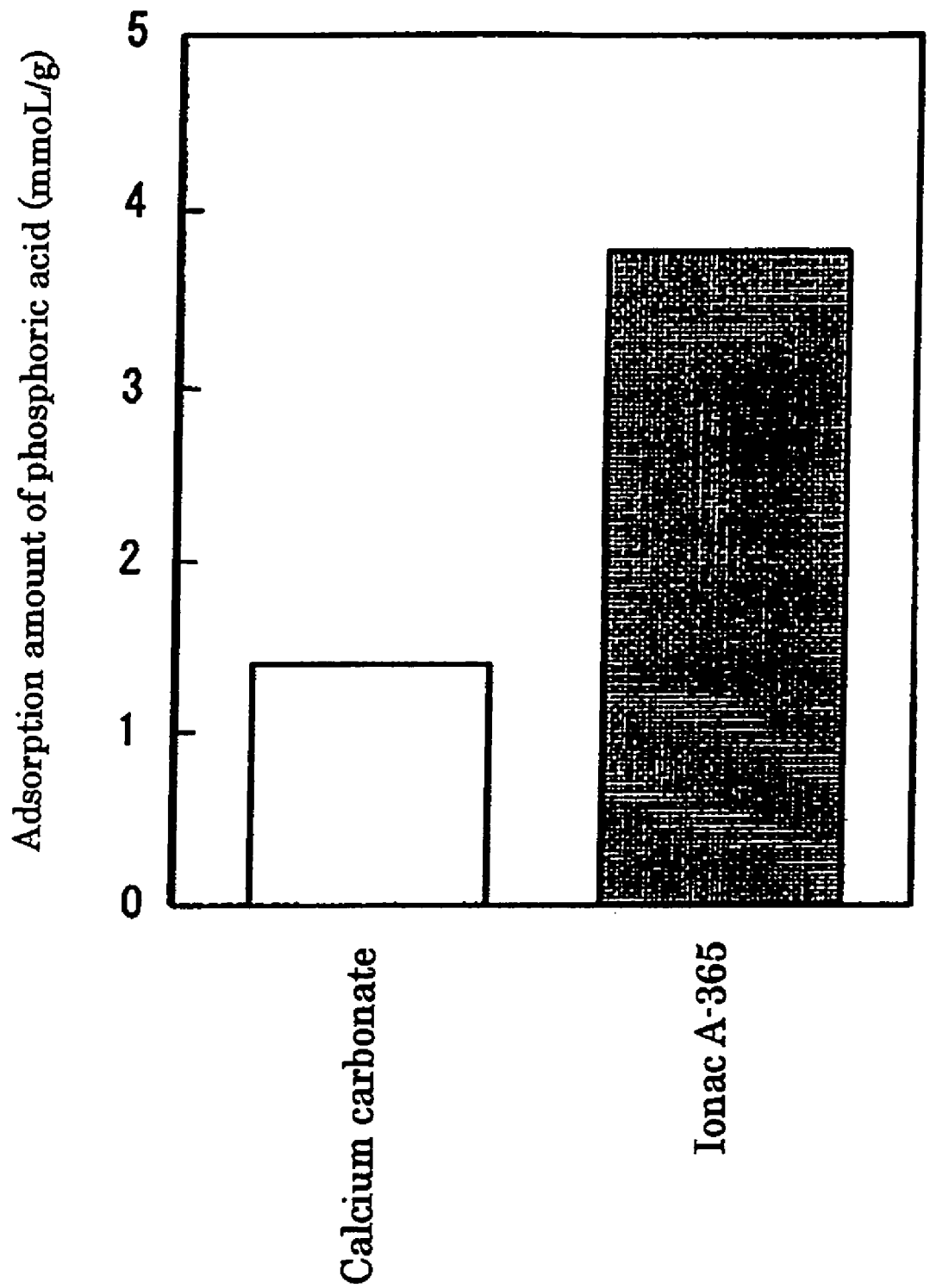
FIG. 1 is a figure which shows the bound amounts with phosphoric acid of the weakly basic anion exchange resin (Ionac A-365; Sybron Chemicals Co.) and that of calcium carbonate with phosphoric acid in Example 1.

In the following described is an embodiment on a phosphate ion adsorbent which uses the above weakly basic anion exchange resin and a preventive and/or a remedy for hyperphosphatemia of the invention.

As a phosphate ion adsorbent and a preventive and/or a remedy for hyperphosphatemia of the invention, although the above ion exchange resin itself can be used as an active ingredient, since this has a particle size of 0.3–1.2 mm, preferably vacuum drying is appllied at room temperature, further being followed by a step of removing impurities with a sieve after pulverization to produce a pharmaceutical composition using an ordinarily used additive for a pharmaceutical preparation. Illustrative of dosage forms of such a pharmaceutical composition are tablets, capsules, fine granules, pills, troches, liquids or the like, and these are administered orally.

An oral pharmaceutical composition can be prepared by ordinarily used conventional methods such as mixing, filling and compressing. Further, by use of a repetitive blend procedure an effective ingredient can be distributed using a large amount of filler in a pharmaceutical composition. For example, tablets or capsules used for oral administration are favorably administered as a dosage unit form, which may contain conventionally used carriers for preparations such as binders, fillers, diluents, compressing agents, lubricants, disintegrators, colorants, flavoring agents and wetting agents. Tablets can be made as coated tablets using, for example, a coating agent according to widely known methods.

Illustrative of preferable fillers are cellulose, mannitol, lactose, etc., and disintegrators such as starch, polyvinylprrolidone and a starch derivative such as sodium starch glycolate or lubricants such as sodium laurylsulfate can be used as additives for preparations. A pharmaceutical composition of an oral liquid form is provided as, for example, aqueous or oil suspensions, solutions, emulsions, syrups or elixirs, or as a dry pharmaceutical composition which can be redissolved before use by water or an appropriate medium.

In such liquids can be blended conventional additives, for example, such as precipitation preventing agents including sorbitol, syrup, methyl cellulose, gelatin, hydroxyethylcellulose, carboxymethylcellulose, aluminum stearate gel or hydrogenated edible fat; emulsifiers such as lecithin, sorbitan monooleate or gum arabic; oily esters such as almond oil, finely distilled coconut oil or glycerin ester; non-aqueous solvents such as propylene glycol or ethyl alcohol (edible oil can also be contained); preservatives such as methyl ester of p-hydroxybenzoic acid or sorbic acid, and conventional flavoring agents or colorants if needed.

In the case of the above oral pharmaceutical compositions, for example, such as tablets, capsules or fine granules, usually contain 5–95 wt. %, preferably 25–90 wt. % of the effective ingredient. The remedy of the invention is useful for prevention and/or treatment of hyperphosphatemia caused by diseases of a renal function disorder and among them, is particularly useful for prevention and/or treatment of hyperphosphatemia accompanied by renal function disorders. The doses of the preventive and/or the remedy for hyperphosphatemia of the invention may appropriately be determined according to the age, health condition, body weight and disease severity of the patient, the kind and frequency of therapy and treatment simultaneously carried out, the nature of the desired effect, and the like. Generally, the daily dose for an adult may be 1-60 g in the active ingredient amount and may be administered once or several times a day.

In the following, the invention is explained concretely by the examples. However, the invention is not limited thereto. Here, Ionac A-365 (trade name; Sybron Chemicals Co.) pulverized and dried for purification as the weakly basic anion exchange resin and calcium carbonate described in Japanese Pharmacopeia were used.

Further, Renagel (Renagel®; manufactured by Geltex Co., U.S.) was used as a comparative drug.

EXAMPLE 1

Adsorption Test of Phosphoric Acid at the Ion Concentration of Intestinal Juice

Considering the ion concentration of intestinal juice, the weakly basic anion exchange resin (Ionac A-365; Sybron Chemicals Co.) or calcium carbonate was added to an aqueous solution in which $NaH_2PO_4$ 5 mM was dissolved in such a way that each became 1 mg/ml, adjusted to pH 6.8 by sodium hydroxide, and stirred at 37° C. for 1 hour. Then, the resin was removed by a filter, and phosphoric acid which was not bound to the resin was measured by an inorganic phosphrus measurement reagent (P Test Wako), whereby the amount of phosphoric acid bound to the resin was calculated based on its value. the results are shown in FIG. 1. Ionac A-365 showed a higher binding amount with phosphoric acid compared with calcium carbonate.

EXAMPLE 2

Effects on Amount of Blood and Urinary Phosphorus in Normal Rats

Using male SD rats (aged 8 weeks), the experiments on suppressive effects for the increase of urinary phosphorus amount in the weakly basic anion exchange resin (Ionac A-365; Sybron Chemicals Co.) or calcium carbonate were carried out as follows.

Figure 2:
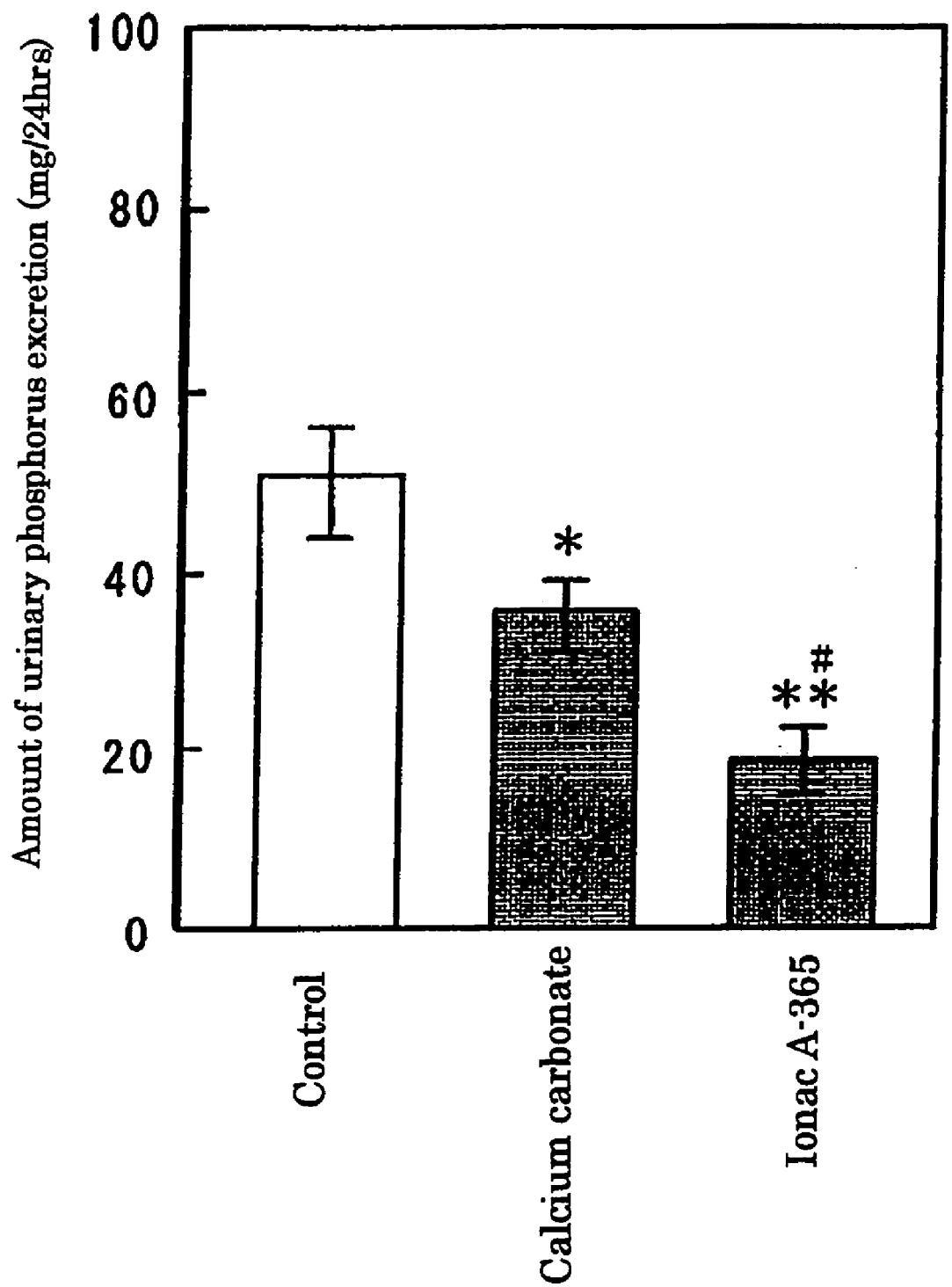
FIG. 2 is a figure which shows the increased amounts of urinary phosphorus excretion calculated from the difference between before and after the drug administration in Example 2; in the figure * and ** show significant differences compared with control ($p<0.05$ and $p<0.01$ respectively, student-t test). Further, in the figure # shows a significant difference compared with the calcium carbonate administration group (($p<0.05$, student-t test).

Namely, after the rats were given with feed (20 g/rat/day) containing 0.3% phosphorus for 7 days, feed (20 g/rat/day) containing 0.58% phosphorus was mixed with 0.5 g of Ionac A-365 or calcium carbonate and the mix feed was further administered to the rats for 5 days. Further, urine was collected for 24 hours before the drug administration and 5 days after the drug administration, and the amount of urinary phosphorus was calculated based on the urinary phosphorus concentration and the amount of urine. The urinary phosphorus concentration was measured by an inorganic phosphorus measurement reagent (P Test Wako). The increased amount of urinary phosphorus excretion was calculated based on the obtained difference of urinary phosphorus amount between before drug administration and 5 days after the drug administration, and compared with that of the non-administration group (control). As for rats in each group, 6 rats in each were subjected to the experiments. The obtained results are shown in FIG. 2. The increase of urinary phosphorus excretion in the calcium carbonate administration was significantly suppressed compared with that of control. Also, although the increase of urinary phosphorus excretion was significantly suppressed in the Ionac A-365 administration group, the effect was larger than that of the calcium carbonate administration group.

EXAMPLE 3

Effects on Blood Phosphorus Concentration and Renal Function in Rats With ⅚ Nephrectomy Using male SD rats (aged 9 weeks), the experiments on the effects for the lowering action of urinary phosphorus amount and the renal function in the weakly basic anion exchange resin (Ionac A-365; Sybron Chemicals. Co.) or calcium carbonate were carried out as follows.

Figure 3:
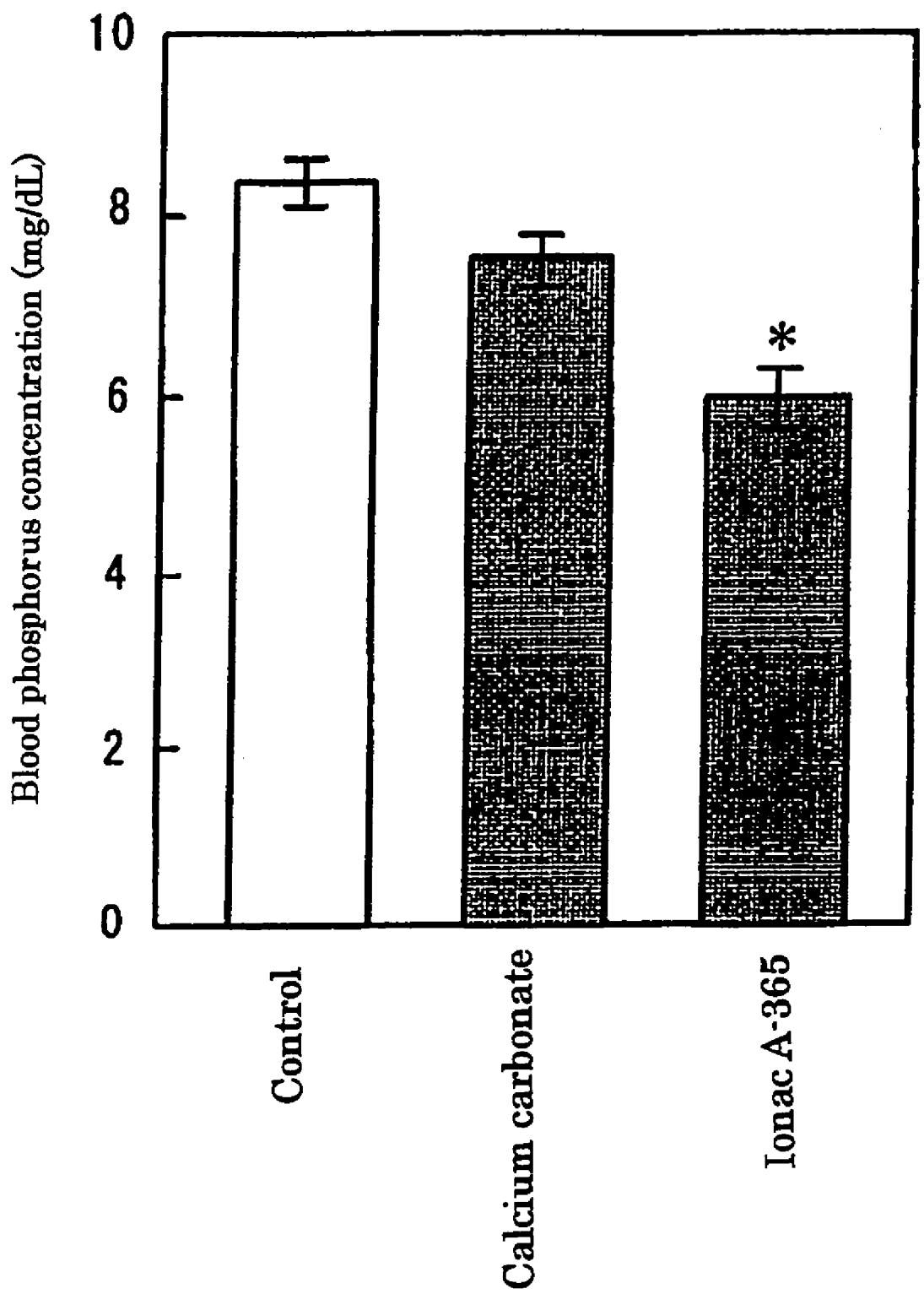
FIG. 3 is a figure which shows the blood phosphorus concentrations after the drug administration in Example 3, and in the figure * shows a significant difference compared with control ($p<0.05$, student-t test).
Figure 4:
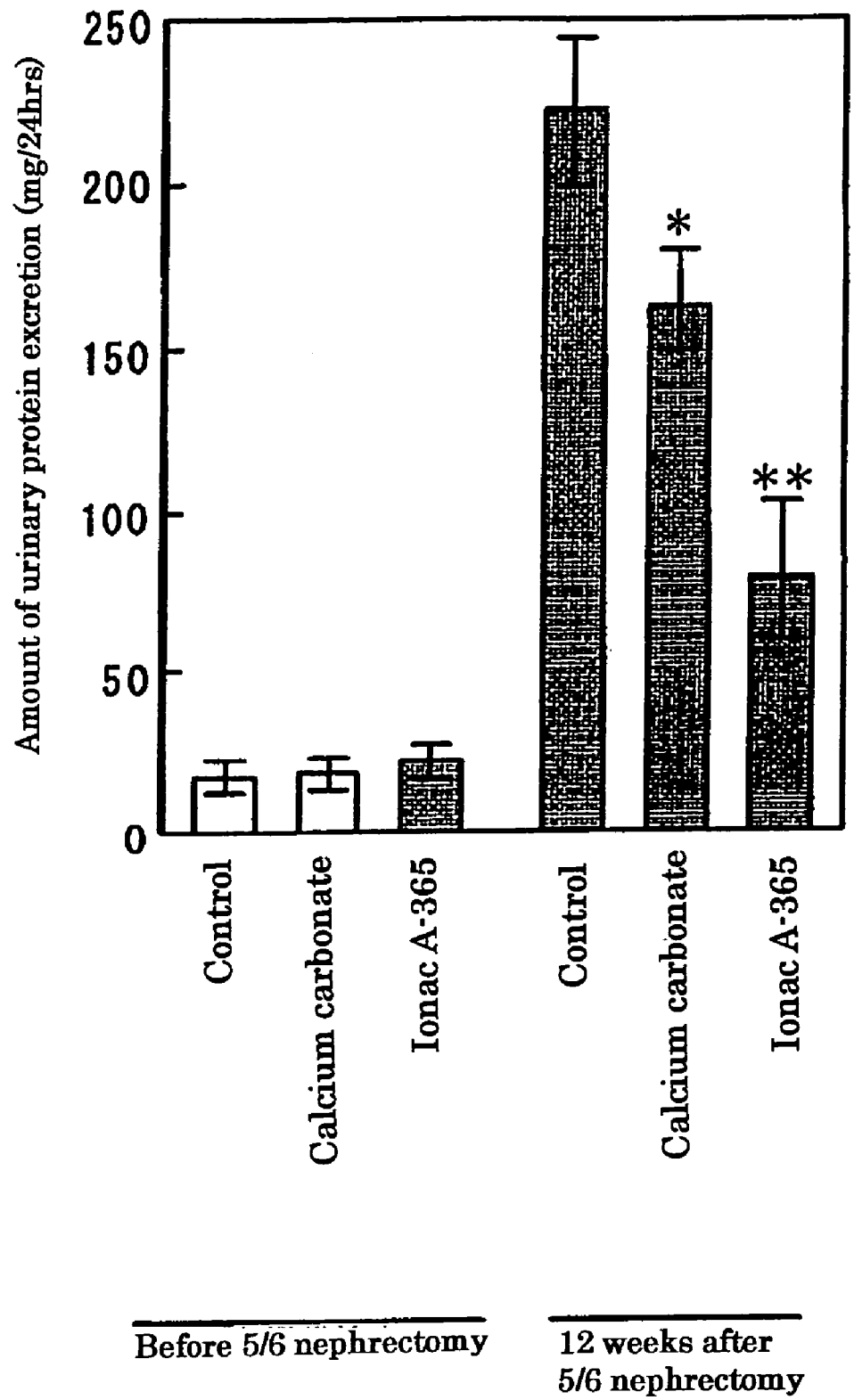
FIG. 4 is a figure which shows the amounts of urinary protein excretion before and after the drug administration in Example 3, and in the figure * and ** show significant differences compared with control ($p<0.05$ and $p<0.01$ respectively, student-t test).

Namely, ⅔ of the left kidney was removed, after 1 week the right kidney being totally removed to make rats with ⅚ nephrectomy. After 1 week, a mixed feed administration of calcium carbonate or Ionac A-365 started. As a powder feed for rat MF manufactured by Oriental Yeast was used, and the administration dose was made 0.3 g content in 15 g of the feed. 12 weeks after the preparation of rats with ⅚ nephrectomy, blood was collected from the caudal vein, and the blood phosphorus concentration was measured by an inorganic phosphorus measurement reagent (P Test Wako). Also, urine was collected for 24 hours before the nephrectomy and 12 weeks after the nephrectomy, and the urinary protein concentration being measured by a protein measurement reagent (Protein Assay Kit, Bio-lad). As for rats in each group, 9 rats in each were subjected to the experiments. The obtained results are shown in FIG. 3 and FIG. 4. As shown in FIG. 3, in the calcium carbonate administration group there was no significant difference in blood phosphorus concentration compared with control. In the Ionac A-365 administration group a significant lowering of blood phosphorus concentration was observed. Also, as shown in FIG. 4, although in control the amount of urinary protein excretion increased remarkably at 12 weeks after preparation of rats with ⅚ nephrectomy and deterioration of kidney function was shown, in the calcium carbonate administration group, the increase of urinary protein excretion amount was significantly suppressed compared with control. Also, in the Ionac A-365 administration group the increase of urinary protein excretion amount was significantly suppressed, its action intensity being larger than that of the calcium carbonate administration group, showing the suppressive effect against deterioration of kidney function.

EXAMPLE 4

Figure 5:
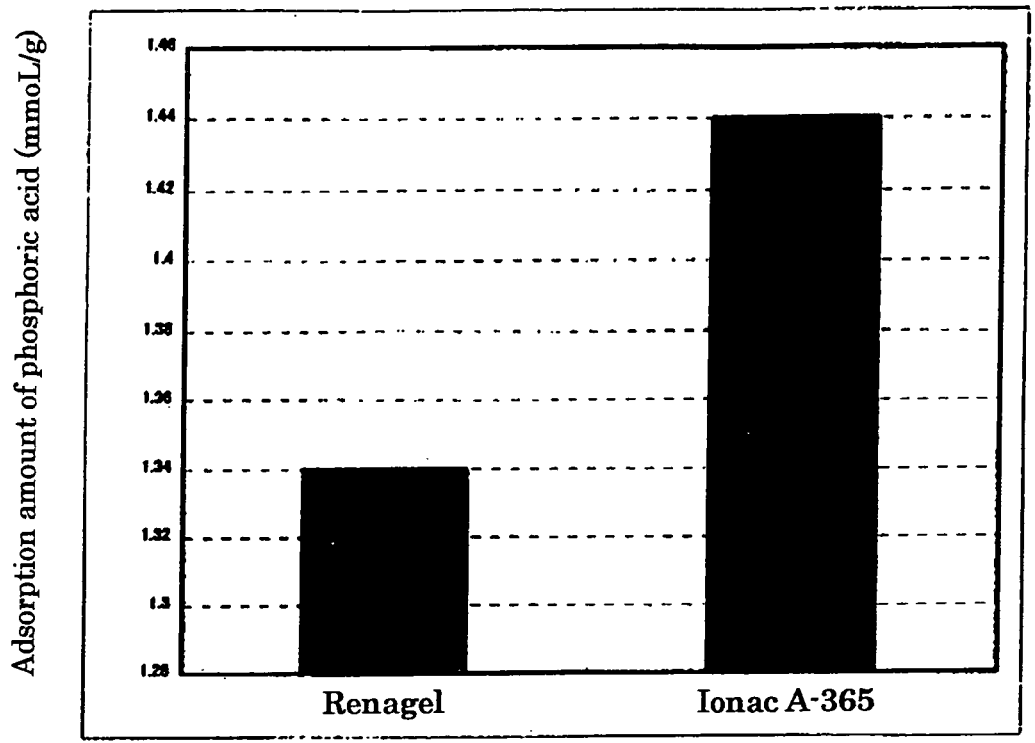
FIG. 5 is a figure which shows the adsorption amounts of phosphoric acid toward Ionac A-365 and Renagel in Example 4.
Figure 6:
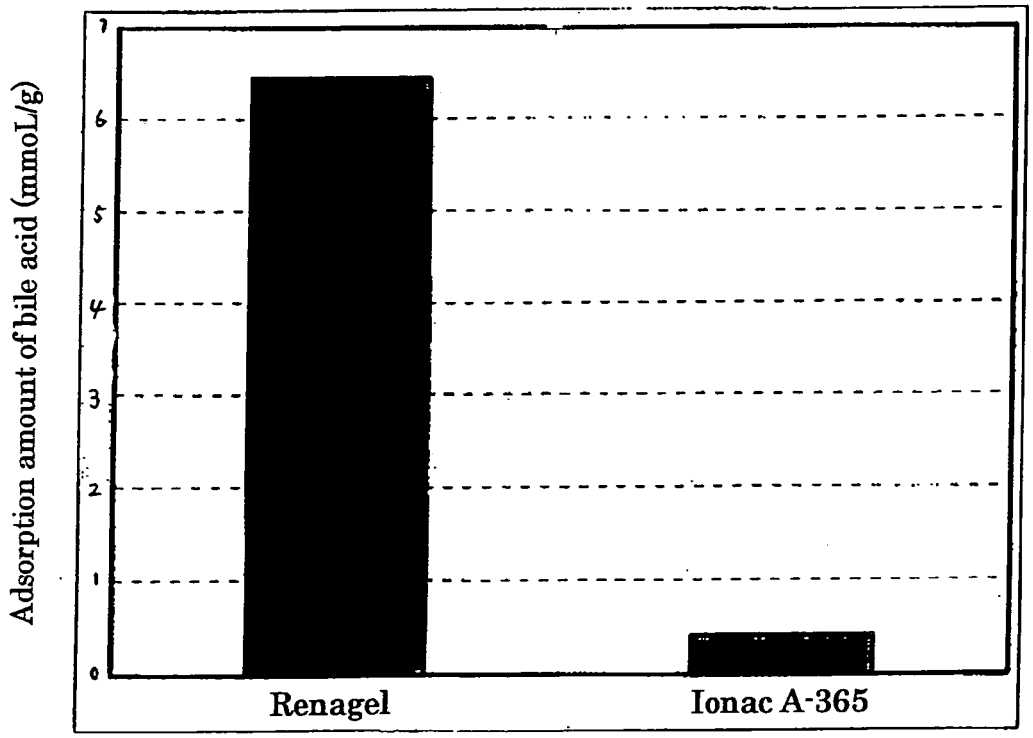
FIG. 6 is a figure which shows the adsorption amounts of bile acid toward Ionac A-365 and Renagel in the example 4.

Effects of High Concentration Bile Acid On Phosphoric Acid Adsorption Specificity With an aim to investigate the effects of a high concentration bile acid on a phosphoric acid adsorption specificity, the adsorption property of an anion exchange resin for phosphate ion and glycolic acid was examined. Considering the ion concentration in intestinal juice prepared were one preparation having been added with Ionac A-365 1 mg/ml to an aqueous solution in which $NaH_2PO_4$ 5 mM and glycolic acid 20 mM was dissolved and another preparation having been added with Renagel 1 mg/ml to an aqueous solution in which $NaH_2PO_4$ 5 mM and glycolic acid 20 mM was dissolved. Each was adjusted to pH 6.8 by sodium hydroxide, and stirred at 37° C. for 1 hour. Then, the resin was removed by an ultrafilter membrane, and the amount of phosphoric acid which was not adsorbed to the resin was measured by an inorganic phosphorus measurement reagent (registered trade mark, P Test Wako; manufactured by Wako Junyaku Kogyo Co.), whereby the amount of phosphoric acid adsorbed and removed by each anion exchange resin was calculated based on this measurement value. Further, the amount of glycolic acid not adsorbed to the resin was measured by a bile acid measurement reagent (registered trade mark, Total Bile Acid Test Wako; manufactured by Wako Junyaku Kogyo Co.), whereby the amount of glycolic acid adsorbed and removed by each anion exchange resin was calculated based on this measurement value. The results are shown in FIG. 5 and FIG. 6. In the presence of bile acid 20 mM Renagel, a control drug (comparative drug), showed a high bile acid adsorption activity. In contrast to this, Ionac A-365 maintained a high phosphoric acid adsorption activity even in the presence of bile acid 20 mM, wherein very little the bile acid adsorption was observed.

INDUSTRIAL APPLICABILITY

It is found out that a weakly basic anion exchange resin which has been used up to now at the industrial level for the purpose of decoloring, demineralization or hazardous substance removal of solvent, a supplied water or a waste water is useful as a phosphate ion adsorbent. Since this remarkably suppresses blood phosphorus concentration and urinary phosphorus excretion, achieving suppression for deterioration of kidney function, it is effective for prevention and/or treatment of hyperphosphatemia and useful as a drug.

The invention claimed is:

1. A method of treating hyperphosphatemia in a patient comprising orally administering to the patient in need of treatment for hyperphosphatemia a therapeutically effective amount of a pharmaceutically acceptable phosphate ion absorbent comprising as an active ingredient a weakly basic anion exchange resin, wherein said resin is a copolymer containing as monomer components divinylbenzene and acrylamide or divinylbenzene and acrylate, wherein the copolymer further contains a tertiary amino group.

2. The method of claim 1 wherein the copolymer further contains as monomer components one or more components selected from the group consisting of acrylonitrile, vinylimidazole, vinylhistidine, vinylpyrazine and diaminophenylmethane.

3. The method of claim 1 wherein the weakly basic anion exchange resin has porous bead structure.

* * * * *